(12) United States Patent
Diong

(10) Patent No.: US 8,100,836 B2
(45) Date of Patent: Jan. 24, 2012

(54) AUGMENTED RIC MODEL OF RESPIRATORY SYSTEMS

(75) Inventor: Billy Ming Diong, Arlington, TX (US)

(73) Assignee: Texas Christian University, Fort Worth, TX (US)

(*) Notice: Subject to any disclaimer, the term of this patent is extended or adjusted under 35 U.S.C. 154(b) by 1448 days.

(21) Appl. No.: 11/634,636

(22) Filed: Dec. 6, 2006

(65) Prior Publication Data

US 2008/0139956 A1 Jun. 12, 2008

(51) Int. Cl.
*A61B 5/08* (2006.01)
(52) U.S. Cl. .................................................. 600/529
(58) Field of Classification Search ........... 600/529–543
See application file for complete search history.

(56) References Cited

U.S. PATENT DOCUMENTS

| | | | | |
|---|---|---|---|---|
| 3,851,641 | A | * | 12/1974 | Toole et al. .................... 600/529 |
| 5,513,648 | A | * | 5/1996 | Jackson ......................... 600/529 |
| 2009/0068627 | A1 | * | 3/2009 | Toly ............................... 434/267 |

OTHER PUBLICATIONS

"Evaluation of Augmented TIC Model of Child Respiratory Impedance Based on Impulse Oscillometry Data", A. Rajagiri and B. Diong, IEEE, Apr. 2006.*
"A Comparison of Various Respiratory System Models Based on Parameter Estimates From Impulse Oscillometry Data" T Woo, B Diong, L Mansfield, M Goldman, P Nava, H Nazeran, Proceedings of the 26th International Conference of the IEEE EMBS, Sep. 1-5, 2004.*
"Evaluation of Respiratory System Models Based on Parameter Estimates from Impulse Oscillometry Data", S Baswa, B Diong, H Nazeran, P Nava, M Goldman, Proceedings of the 2005 IEEE Engineering in Medicine and Biology 27th Annual Conference, Sep. 1-4, 2005.*
"Modeling Human Respiratory Impedance", Bill Diong, Homayoun Nazeran, Patricia Nava, Michael Goldman, IEEE Engineering in Medicine and Biology Magazine Jan./Feb. 2007.*
"Can Asthma in Children be Detected by the Estimated Parameter Values of the Augmented RIC Model?" A Rajagiri, B. Diong, M. Goldman, H. Nazeran, Proceedings of the 28th IEEE EMBS Annual International Conference, Aug. 30-Sep. 3, 2006.*
"Input Impedance, Wave Travel, and Reflections in the Human Pulmonary Arterial Tree: Studies Using an Electrical Analog" GH Pollack, RV Reddy, A Noordergraaf, IEEE Transactions on Bio-Medical Engineering, Vo. BME-15, No. 3, Jul. 1968.*

(Continued)

*Primary Examiner* — Patricia Mallari
*Assistant Examiner* — Karen Toth
(74) *Attorney, Agent, or Firm* — Charles D. Gunter, Jr.

(57) ABSTRACT

The present invention generally relates to an apparatus and method analyzing the respiratory characteristics of a human respiratory system from impulse oscillometry data, through the use of a linear network of electrical components. The present invention offers an improved alternative to the RIC respiratory circuit model, with an addition of a peripheral resistance to account for the resistance presented by the respiratory system's small airways and of a capacitor to account for extrathoracic compliance. After air pressure and air flow measurements are obtained from the subject by performing Impulse Oscillometry System testing, a graphical representation of a mechanical impedance characteristic may be derived. This allows for the estimation and adjustment of parameter values of the linear network whose components correlate to the resistances, compliances and inertances inherent in the respiratory system. Additionally, the linear network of electrical components may be configured as a virtual network represented in graphical form wherein the parameter values are estimated and adjusted according to program instructions operating on a computer system. The linear network of electrical components serves to provide parametric means for detection, diagnosis and treatment of various pathologies in the human respiratory system.

6 Claims, 4 Drawing Sheets

OTHER PUBLICATIONS

"Oscillation Mechanics of Lungs and Chest in Man," Arthur B. DuBois, et al., Graduate School of Medicine, University of Pennsylvania, Philadelphia, PA, pp. 587-594.

"Statistical Measures of Parameter Est Models Fit to Respiratory Impedance Data: Emphasis on Joint Variabilities," Kenneth R. Lutchen, et al., IEEE Transactions on Biomedical Engineering, pp. 1000-1009, copyright 1986.

"Computer Simulation of the Measured Respiratory Impedance in Newborn Infants and the Effect of the Measurement Equipment," M. Schmidt, et al., Medical Engineering & Physics 20, pp. 220-228, copyright 1998.

"Evaluation of Impulse Oscillation System: Comparison with Forced Oscillation Technique and Body Plethysmography," J. Hellinckx, et al., European Respiratory Journal, pp. 564-570, copyright 2001.

"Lung Ventilatory Performance Pressure-Volume Model, and Parametric Simulation for Disease Detection," Dhanjoo N. Ghista, Proceedings, 19th International Conference—IEEE/EMBS, Chicago, Illinois, pp. 2165-2167, copyright 1997.

"Computer-Controlled Mechanical Simulation of the Artificially Ventilated Human Respiratory System," Samir Mesie, et al., IEEE Transactions on Biomedical Engineering, vol. 50, No. 6, pp. 731-743, copyright 2003.

* cited by examiner

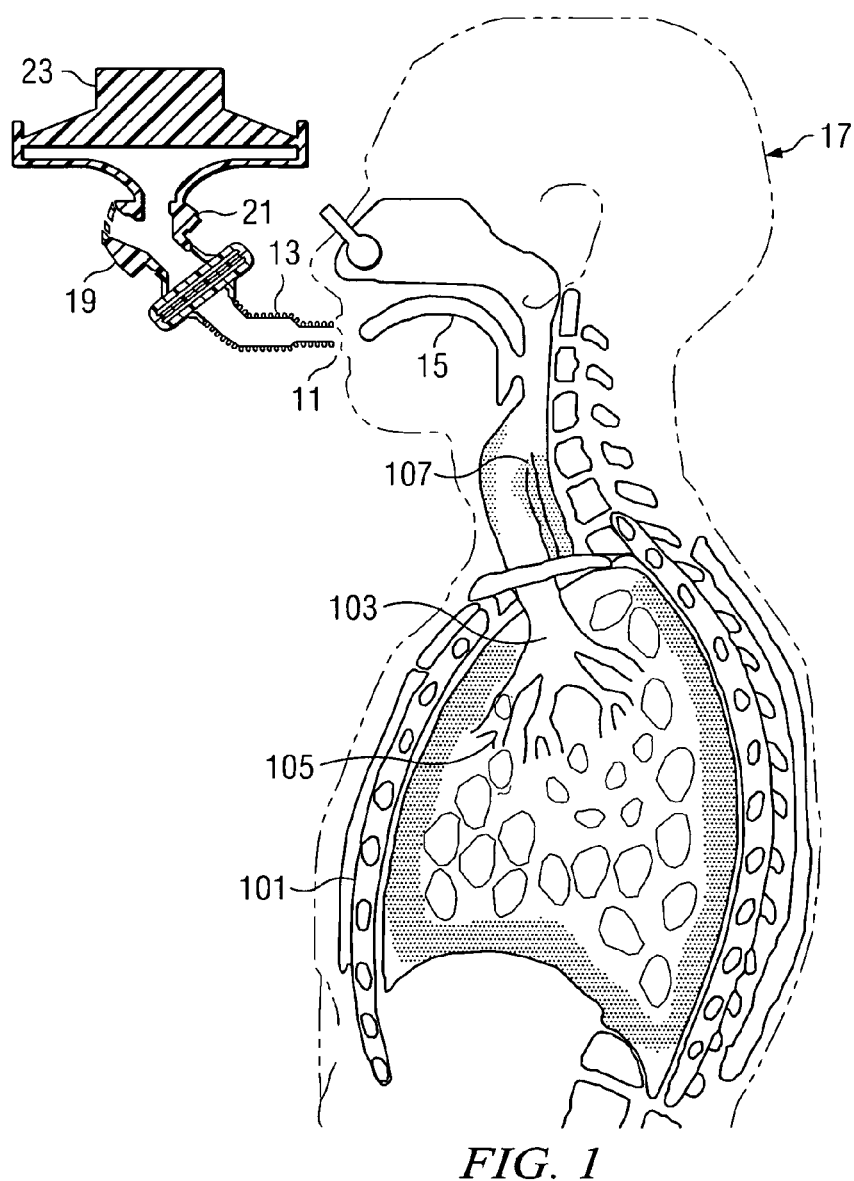
FIG. 1
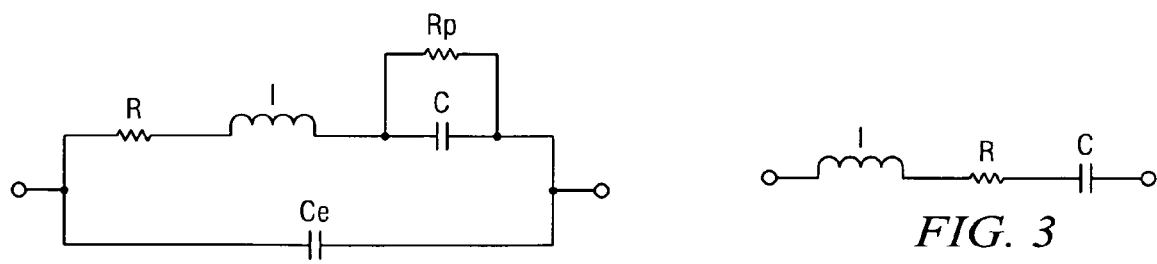
FIG. 2
FIG. 3

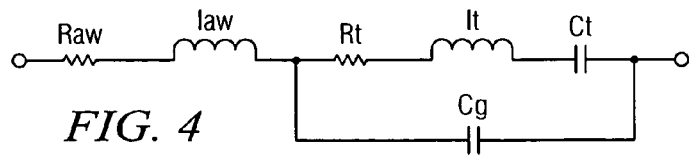
FIG. 4
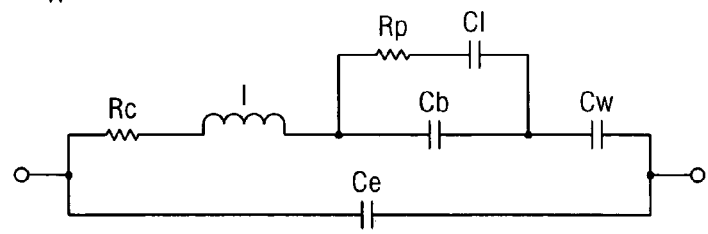
FIG. 5
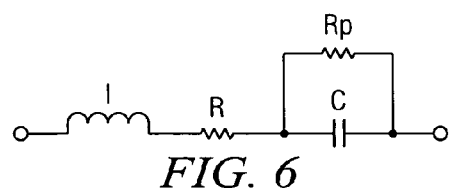
FIG. 6
FIG. 7A
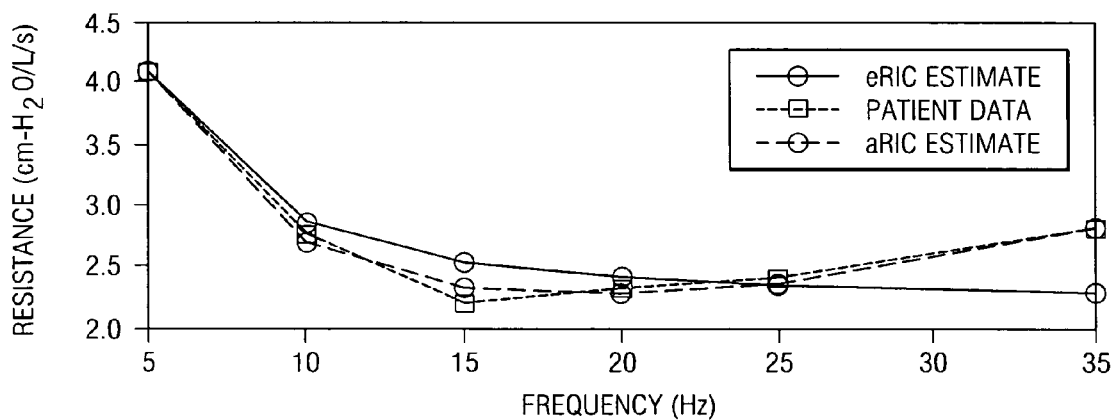
FIG. 7B
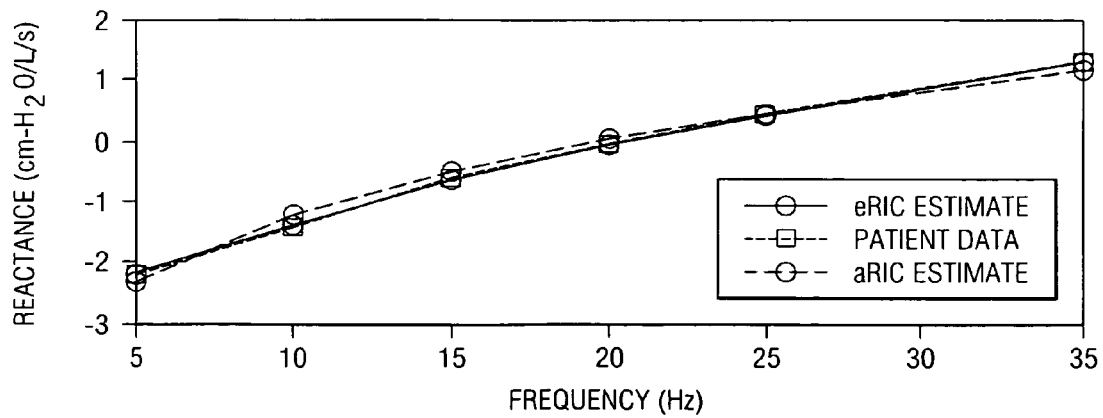

AUGMENTED RIC MODEL OF RESPIRATORY SYSTEMS

BACKGROUND OF THE INVENTION

1. Field of the Invention

The present invention relates generally to an apparatus and method to model mammalian respiratory systems, whereby appropriate computational processing of the estimated component values for such a model can serve as parametric means for detection, diagnosis and treatment of various pathologies.

2. Description of the Prior Art

Pulmonary function tests, spirometry measurements, and lung volume measurements are all examples of various existing alternatives administered for the purposes of testing and assessing human lung conditions. These tests are often useful in diagnosing certain types of lung disease, especially asthma, bronchitis, and emphysema. They are also used after the administration of medications to assess their effect, and to measure progress in a disease treatment. Traditionally, lung function is most commonly assessed by standard spirometric pulmonary function tests. However, spirometric measurements require maximal coordinated inspiratory and expiratory efforts by the tested subject. Such considerable degree of cooperation required from the subject makes spirometry inappropriate for young children and older adults. In contrast, respiratory function assessment by the method of forced oscillation requires minimal patient cooperation, namely wearing a nose clip to close the nares and breathing normally through the mouth. Air pressure and rate of air flow at the entrance to the respiratory system are measured, thereby defining its mechanical impedance. In particular, the Impulse Oscillometry System (IOS) is a commercially available product for measuring respiratory impedance by employing brief (60-70 milliseconds) pulses of pressure using a loudspeaker. IOS measurements yield frequency-dependent impedance curves that, in clinical practice today, are inspected to identify changes in shape, or course, and magnitude from those produced in a healthy state.

The impedance curves (one representing the complex impedance's real part referred to as respiratory resistance $Z_r$, and the other representing the impedance's imaginary part referred to as respiratory reactance $Z_x$) yielded from the IOS measurements are also readily amenable to engineering analysis, and may be correlated with models consisting of electrical components that are analogous to the resistances, compliances and inertances inherent in the respiratory system. With appropriate computational processing, the estimated component values for such respiratory system models can be used as parametric means for better detection, diagnosis and treatment of various pathologies. There are four well-known (linear) models of the human respiratory system, of the type discussed above, each of which seeks to provide an accurate circuit that mimics results obtained from a subject. These models, namely the RIC, viscoelastic, DuBois and Mead models, have been documented extensively in literature, and are summarized as the following:

RIC model—The resistance of the airways R, lung inertance I, and the compliance of the alveoli C, are modeled as a simple three element circuit (with R typically in $cmH_2O/L/s$ or $kPa/L/s$, I in $cmH_2O/L/s^2$ or $kPa/L/s^2$, and C in $L/cmH_2O$ or $L/kPa$). See FIG. 3.

Viscoelastic model—The viscoelastic model parameterizes the respiratory system based on overall airway resistance $R_{aw}$, static compliance $C_s$, and viscoelastic tissue resistance and compliance, $R_{ve}$ and $C_{ve}$, respectively. See FIG. 11.

DuBois model—This model divides the resistance, inertance and compliance properties into separate parameters for the airway and tissue resistance ($R_{aw}$, $R_t$) components. Thus the model includes separate parameters for inertance ($I_{aw}$, $I_t$), and alveolar and tissue compliance ($C_g$, $C_t$). See FIG. 4.

Mead model—Mead's model simulates different mechanics in the lung and chest wall. Its seven parameters are inertance (I), central and peripheral resistance ($R_c$ and $R_p$), and lung, chest wall, bronchial tube, and extrathoracic compliance ($C_l$, $C_w$, $C_b$, $C_e$). See FIG. 5.

For each of the above models, values for that model's parameters needed to be determined to minimize the difference between measured impedance data (at discrete frequencies) and the impedance produced by those model parameter values. This optimization procedure is referred to as parameter estimation, which is similar in concept to curve-fitting. Error criteria that are commonly used in parameter estimation problems include least absolute value (LAV), least squares (LS), minimax, and maximum likelihood.

In the patent literature, U.S. Pat. No. 6,068,602, to Tham et al., includes a discussion of electrical circuit models of mammalian respiratory systems including a method and apparatus for determining airway resistance and lung compliance. More specifically, Tham et al. teach the use of electrical circuit models wherein at least one component parameter is non-linear. The system non-intrusively obtains pressure and flow data signals from a pressure transducer and a laminar flow element without interrupting or interfering with normal breathing and gas supply to a patient. An invariant exponential is determined empirically based on physical characteristics of the airway. The non-linear airway resistance and lung compliance can then be calculated based on the sensed flow rate, gas pressure, a calculated gas volume, and the invariant exponential using linear techniques.

However, despite current progress in the field of respiratory analysis, such as that taught in the Tham et al. reference, there is a continuing need to provide reliable circuit models capable of accurately simulating the respiration system of a subject.

A need exists for an improved circuit model that further minimizes the differences between the measured impedance data and the impedance produced by the model parameter values.

A need also exists for a method of analyzing a subject's air pressure and air flow that is non-invasive and easily administered to subjects of all ages and health.

SUMMARY OF THE INVENTION

The present invention provides a method and apparatus for analyzing the respiratory characteristics of a human respiratory system. In one aspect, the apparatus of the invention is a respiratory impedance model for use in analyzing impulse oscillometry data for a human subject. The impedance model is a linear network of electrical components connected in series between first and second terminals including a first resistance, a first inductance and a first capacitance respectively corresponding to the central resistance of the airways, the lung inertance and the alveoli compliance of a human respiratory system. Additionally, there is a second resistance component connected directly across the first capacitance component and corresponding to the peripheral resistance of the alveoli in the small airways of the lungs, and a second capacitance component connected between the first and second terminals corresponding to an extrathoracic compliance parameter of the human respiratory system.

The method of the present invention includes the following steps: First, a mechanical impedance characteristic is obtained from measured impulse oscillometry data values, taken at a plurality of test frequencies, of air pressure and air flow at the entrance to the respiratory system of a human subject. In order to attain these values, an impulse oscillometry device is first coupled to the subject. The impulse oscillometry device then generates a predetermined sequence of impulse test signals at the plurality of test frequencies, and measurements are taken of air pressure and air flow parameters for each of the sequence of impulse test signals. A graphical representation of the mechanical impedance characteristic is then derived from the measured impulse oscillometry data.

Next, a linear network analogue of the human respiratory system, as described above, is applied. Now, parameter values of the linear network analogue of electrical components may be estimated to produce an electrical impedance analogue that matches the measured mechanical impedance characteristic within a predetermined tolerance over the frequency range of at least 5 to 35 Hz. and wherein the compliance parameter values are less than 10 liter/cmH$_2$O. The predetermined tolerance is expressed as an error criterion selected from the group consisting of the methods of absolute value, least squares, minimax, and maximum likelihood. In the preferred embodiment of the present invention, the error criterion is a least squares method defined as the weighted sum of the squared differences between the estimated parameters and the measured sample values wherein the sum is weighted by the frequency of occurrence of the sample values. In order to finalize the parameter values of the linear network, it is necessary to make initial estimates of the parameter values using a random number generator and then adjust the initial estimates of the parameter values to conform the complex impedance between the first and second terminals to the mechanical impedance characteristic obtained from the impulse oscillometry measurements.

Finally, computational processing is applied to the estimated parameter values of the linear network analogue for performing detection, diagnosis and treatment of respiratory pathologies. The method of the present invention includes the effects of peripheral resistance of the small airways and of extrathoracic compliance of the respiratory system.

The linear network may be configured as an assembly of physical components supported on a frame, wherein each of the physical components is adjustable within a range of parameter values. The first and second terminals are connectable to a signal generator and an instrument for measuring complex impedance. Alternatively, the linear network may be configured as a virtual network represented in graphical form and wherein the parameter values are estimated and adjusted according to program instruction operating on a computer.

Additional objects, features and advantages will be apparent in the written description which follows.

BRIEF DESCRIPTION OF THE DRAWINGS

FIG. 1 is a simplified diagram outlining the process of measuring the respiratory impedance by the forced oscillation method, specifically the Impulse Oscillometry System used in the present invention.

FIG. 2 is a circuit schematic of the circuit modeling approach encompassed in the system of the present invention, referred to as the augmented RIC model.

FIG. 3 is a circuit schematic of the circuit modeling approach encompassed by the traditional RIC model (Prior Art).

FIG. 4 is a circuit schematic of the circuit modeling approach encompassed by the DuBois model (Prior Art).

FIG. 5 is a circuit schematic of the circuit modeling approach encompassed by the Mead model (Prior Art).

FIG. 6 is a circuit schematic of the circuit modeling approach encompassed by the extended RIC model.

FIGS. 7A and 7B are a graphical analysis of resistance ($Z_R$) and reactance ($Z_X$) plots for one patient using parameter estimates for the augmented RIC model and for the extended RIC model.

DETAILED DESCRIPTION OF THE INVENTION

The present invention is directed towards providing a method and apparatus for analyzing the respiratory characteristics of a human respiratory system from impulse oscillometry data (10D). Turning to FIG. 1, there is shown a simplified side-view diagram outlining the human respiratory system, specifically the lungs which are shown at 101. The following is a brief explanation concerning the anatomy of the human lungs, as it pertains to the field of the present invention. When an individual breathes in, whether through the mouth or nose, air travels down the trachea 107 and into the lungs 101 through various airways known as bronchial tubes 103. Lungs 101 are covered with millions of tiny air sacs called alveoli 105, which fill with air, causing the lungs 101 to become larger. Each alveoli 105 is covered with tiny blood vessels, called capillaries, which assist in releasing carbon dioxide from the blood stream while replenishing oxygen to the blood flowing back to the heart. There are large airways towards the entrance to the lungs, which begin to taper into narrow smaller airways towards the extremities of the lungs 101. It is important to note that both the large and small airways contain alveoli 105.

Figure 11:
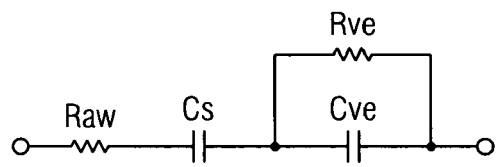
FIG. 11 is a circuit schematic of the circuit modeling approach encompassed by the viscoelastic model (Prior Art).

As previously discussed in the Description of the Prior Art, there are four well-known (linear) circuit models of the human respiratory system, namely the RIC (FIG. 3), viscoelastic (FIG. 11), DuBois (FIG. 4) and Mead models (FIG. 5). The RIC model, shown in FIG. 3, uses three components, namely a resistor, an inductor and a capacitor, to represent the resistance of the airways, lung inertance, and the compliance of the alveoli respectively. The inductor corresponding to the lung inertance I is commonly measured in cmH$_2$O/L/s$^2$ or kPa/L/s$^2$, the resistor corresponding to the resistance of the airways R is measured in cmH$_2$O/L/s or kPa/L/s, and the capacitor corresponding to the compliance of the alveoli C is measured in L/cmH$_2$O or L/kPa.

The augmented RIC model of the present invention, illustrated in FIG. 2, is proposed as an improvement to the RIC model of FIG. 3, or more specifically, an improvement to the extended RIC model illustrated in FIG. 6 of the drawings, as will now briefly be explained. The extended RIC model, illustrated in FIG. 6, follows the same layout of the RIC model (FIG. 3), namely the use of an inductor corresponding to the lung inertance I, a resistor corresponding to the resistance of the airways R and a capacitor corresponding to the compliance of the alveoli C. The extended RIC model, developed by the present inventor, improves upon the RIC model by adding the $R_p$ component, intended to represent the peripheral resistance component in the respiratory system's small airways. However, even the extended RIC model exhibits a monotonic real component of the mechanical impedance characteristic which does not correspond with the observed respiratory system behavior at the higher frequencies due to upper airways shunt effects.

Applicant's invention provides an improved apparatus and method for accurately and reliably modeling the human respiratory system, through the use of a linear network of electrical components, of the same general type as those discussed above. The augmented RIC model (see FIG. 2) builds on the extended RIC model shown in FIG. 6. Each component from the extended RIC model is present in the augmented RIC model, yet additional features provide an improved design that is capable of rendering a more accurate model of the human respiratory system. The augmented RIC model resulted from experimental efforts to overcome the inability of the prior art models to exhibit a rise in the real part of the mechanical impedance at frequencies above approximately 25 Hz that is typical of human patient data.

The linear network of electrical components of the augmented RIC is comprised of 5 electrical components, located between two terminals. A resistor R (see FIG. 2) is operatively connected to the first terminal, and corresponds to the central resistance of the airways. An inductor I is connected in series to the resistor R, and corresponds to the lung inertance. A first capacitor C is connected in series with the inductor I and the second terminal, and represents the compliance of the alveoli. In the improved circuit of the invention; a second resistor $R_p$ is operatively connected directly in parallel with the first capacitor C, and corresponds to the peripheral resistance in the small airways of the respiratory system. Lastly, a second capacitor $C_e$ connects across the network, or from the first terminal to the second terminal. $C_e$ functions to represent the extrathoracic compliance of the alveoli in the small upper airways of the respiratory system. It should be noted that the central resistance R may be defined as the "primary" resistance, and the peripheral resistance $R_p$ may similarly be defined as the "secondary" resistance. The resistors R and $R_p$ are measured in $cmH_2O/L/s$ or $kPa/L/s$, the inductor I is measured in $cmH_2O/L/s^2$ or $kPa/L/s^2$, and the capacitors C and $C_e$ are measured in $L/cmH_2O$ or $L/kPa$.

The peripheral resistance $R_p$, found in both the extended and augmented RIC models, allows for the observed frequency dependence of the real component of typical impedance data, which is beyond the RIC model's capability (it predicts a frequency-independent constant real impedance equal to R). The physical justification for this additional resistive element is that it models the resistance presented by the respiratory system's small airways. Further, the augmented RIC model includes an additional element $C_e$ to model extrathoracic compliance found in the upper airways of the respiratory system. The addition of $C_e$ allows the real part of the respiratory system's impedance to increase at the higher frequencies due to upper airways shunt effects, as observed in a significant portion of the Impulse Oscillometry System (IOS) data analyzed in detail below. The inclusion of $R_p$ and $C_e$ serves to lessen the magnitude of modeling error found between the subject data and the model's estimated parameters, thereby providing an improved alternative for respiratory system models.

It should be noted that the linear network of electrical components may be configured as an assembly of physical components supported on a frame. In this embodiment, each of the physical components would be adjustable within a range of parameter values. The first and second terminals could then be connected to a signal generator and an instrument for measuring complex impedance. In an alternative embodiment, the linear network could be configured as a virtual network represented in graphical form. In this embodiment, the parameter values may be estimated and adjusted according to program instructions operating on a computer system.

A primary concept, namely that a suitable model for evaluating and diagnosing respiratory function must enable a relatively close fit to impulse oscillometry data and also be comprised of realistic parameter values, led to the design of the augmented RIC model. It is important to note that this concept, as well as the resulting augmented RIC design, arose after evaluating the four known respiratory impedance models, as well as one experimental model (the extended RIC model), for the human respiratory system.

The operation of the apparatus and method of the invention will now be further described. To begin the modeling process, it is first necessary to obtain measurements of air pressure and also rate of air flow at the entrance of the respiratory system of the subject. The method of the present invention begins by obtaining a mechanical impedance characteristic for the respiratory system from measured impulse oscillometry data values, taken at a plurality of test frequencies, of air pressure and air flow at the entrance to the respiratory system of the subject. It is first necessary to couple the impulse oscillometry system to the subject. With reference to FIG. 1, the impulse oscillometry system contains a mouthpiece 11 that connects an airway 13 to the entranceway 15 of the respiratory system of a human subject 17. Additionally, there is a breathing gas flow rate sensor 19 and breathing gas pressure sensor 21 attached to the airway 13 to sense gas flow and gas pressure therein and produce a flow rate and pressure signal therefrom. An analog to digital converter receives the analog signals from the gas flow rate sensor and the gas pressure sensor and produces a digital signal in response. An analyzer, such as a computer, is then connected to the A/D converter to receive the digital signals and calculate a mechanical impedance characteristic of the resistance and compliance of the airway, including the small airways, of the subject.

In the preferred embodiment of the present invention, the IOS technique is used to measure respiratory impedance by employing brief (60-70 milliseconds) pulses of pressure using a loudspeaker 23, as shown in FIG. 1. The impulse oscillometry device generates a predetermined sequence of impulse test signals at a plurality of test frequencies, wherein air pressure and air flow parameters are measured for each of the sequence of impulse test signals. IOS is effort independent, as brief pressure pulses are applied during tidal breathing. The pressure-flow oscillations are superimposed on the subject's tidal breaths, and real-time recordings are used to provide an estimate of total respiratory system impedance and its two components, resistance and reactance. IOS has been used to measure short-term changes in bronchial tone in bronchodilator testing and has been shown to correlate with airway resistance ($R_{aw}$) determined by body plethysmography. The IOS technique provides the advantage of requiring only passive cooperation during tidal breathing and does not cause respiratory fatigue.

IOS measurements are used to derive a graphical representation of a mechanical impedance characteristic that, in clinical practice today, may be inspected to identify changes in shape, or course, and magnitude from their healthy state. That is, once the measurements are completed, a mechanical impedance characteristic is derived by Fast Fourier Transform (FFT) from the values of air pressure and rate of air flow at the entrance to the respiratory system. The mechanical impedance curves can also be correlated with respiratory system models consisting of a linear network of electrical components that are analogous to the resistances, compliances and inertances inherent in the respiratory system. Impedance (Z) is the total opposition to current flow in an electrical circuit. The impedance of an inductor is given by the formula:

$$Z_{Inductor} = j\omega I$$

The impedance of a capacitor is given by the formula:

$$Z_{Capacitor} = 1/(j\omega C)$$

Lastly, the impedance of a resistor is given by the formula:

$$Z_{Resistor} = R$$

Note that in each of formulations in this discussion, j is the imaginary number representing the square-root of negative one and ω represents frequency. Thus the total complex impedance of the augmented RIC model is defined by the formula:

$$Z = \{(A(RA + R_p))/$$
$$\{[A(1 - \omega^2 IC_e) + (\omega^2 R_p^2 CC_e)]^2 + [\omega C_e(RA + R_p)]^2\}\} +$$
$$\{j\{\omega(IA - R_p^2 C)[A - \omega^2 C_e(IA - R_p^2 C)] - \omega C_e(RA + R_p)^2\}/$$
$$\{[A(1 - \omega^2 IC_e) + (\omega^2 R_p^2 CC_e)]^2 + [\omega C_e(RA + R_p)]^2\}\}$$

where $$A = 1 + (\omega R_p C)^2$$

Eventually, computational processing may be applied to the estimated parameter values of the linear network for performing detection, diagnosis and treatment of various pathologies. Before beginning the computational processing, however, values for the model parameters need to be determined in order to produce an electrical impedance analogue that matches the measured mechanical impedance characteristic within a predetermined tolerance over the frequency range of at least 5 to 35 Hz. and wherein the compliance parameter values are less than 10 liter/cmH$_2$O. It is vitally important to provide a model that represents the respiratory system as accurately as possible in order to obtain reliable data through its use. The estimation procedure begins by making initial estimates of the parameter values using a random number generator. It is then possible to adjust the initial estimates of the parameter values to conform the complex impedance between the first and second terminals to the mechanical impedance characteristic obtained from the impulse oscillometry measurements. This optimization procedure is referred to as parameter estimation, which is similar in concept to curve-fitting. During the estimation process, it is necessary to express the predetermined tolerance as an error criterion. Therefore, it is necessary to first select a suitable error criterion E that is to be minimized, where $$E = g\{f_1(x), f_2(x), \ldots, f_m(x)\}$$

in which $f_1(x), f_2(x), \ldots, f_m(x)$ are functions involving the n-vector x of parameters $x_1, x_2, \ldots, x_n$ and the independent variables, e.g., frequency, of the m data samples. As has been briefly mentioned, error criteria that are commonly used in parameter estimation problems include least absolute value (LAV), least squares (LS), minimax and maximum likelihood. The LAV criterion is effective in dealing with data outliers and is nearly as accurate as LS for data with normally distributed errors, while the minimax function minimizes the maximum element. But the LS criterion is by far the most commonly used for curve fitting and parameter estimation, and is used in the preferred embodiment of the present invention. In its generalized form, the LS criterion $$\min[E = \Sigma\{w_i f_i(x)\}^2] \text{ in which the sum } \Sigma \text{ is calculated from } i=1 \text{ to } m$$

minimizes the weighted (by factors $w_i$) sum of the squared errors (differences from the m data samples). The least squares method may be defined as the weighted sum of the squared differences between the estimated parameters and the measured sample values wherein the sum is weighted by the frequency of occurrence of the sample values. The least squares method was chosen for this work due to its commonplace use, its relation with other system identification algorithms, and its availability in different software packages.

A linear LS algorithm and a nonlinear LS algorithm (both are descent-based) may be used to estimate the parameters of the respiratory model. The former, as exemplified by Matlab's least squares "lsqlin" program, can be applied to relatively simple functions and is most appropriately used for the RIC model. The latter, as exemplified by Matlab's least squares non-linear "lsqnonlin" program, is necessary for the other models, including the augmented RIC model of the present invention, because of the nonlinear dependence of their impedance functions on the parameters. Unlike the linear LS algorithm, the nonlinear LS algorithm may produce parameter estimates corresponding to a local rather than a global error minimum. To circumvent this problem, a procedure is used whereby each estimation run begins with an initial guess, i.e., a parameter estimate vector produced by a random number generator that's appropriately weighted. This is then repeated many more times, typically twenty-four, per model for each test data to find the parameters estimates yielding the least total estimation error, defined herein as the square root of the sum of the least square equally-weighted real and imaginary impedance estimation errors. This total error value thereby provides an overall measure of "goodness of fit" for the models. Furthermore, this measure is used on the results for both normal subjects and patients with lung disease so as to assess the degree of applicability of a given model to both healthy and ill persons.

The augmented RIC model (FIG. 2) of the present invention has been compared with the performance of the RIC (FIG. 3), extended RIC (FIG. 6), DuBois (FIG. 4) and Mead (FIG. 5) models by estimating their parameters and calculating the corresponding estimation errors. The following results were obtained from IOS data for each test subject belonging to a sample of 5 adults (2 male and 3 female, age 54 to 66 years, weight 60 to 86.8 kg, height 1.60 to 1.80 m) diagnosed with mild obstructive lung disease (bronchiectasis) and another sample of 5 healthy adults (all male, age 33 to 65 years, weight 72.7 to 117.3 kg, height 1.73 to 1.91 m). The data for each test subject were separated into two groups: real impedance $Z_R$ and imaginary impedance $Z_X$. The data samples were at 5, 10, 15, 20, 25 and 35 Hz for both $Z_R$ and $Z_X$. These data were collected recently in the U.S. and Australia, resulting from several visits and multiple tests during each visit of the same patient, and will be referred to as the adult cohort 1 data set. Data for the patient group in this cohort include responses to inhalation of dry powdered mannitol, to assess their provocability prior to institution of treatment with mannitol to improve clearance of secretions, in addition to baseline measurements. Dry powdered mannitol provides an osmotic stimulus to the airway mucosa, which commonly results in increased central and/or peripheral airway resistance. It is an example of the type of "bronchial challenges", the responses of which need to be modeled accurately for treatment purposes.

For the RIC model, estimation of R was a one-dimensional optimization problem and estimation of I and C a two-dimensional optimization problem that were both solved using the linear LS algorithm to determine the optimal R, I and C values.

As mentioned above, to determine parameter estimates for the extended RIC, augmented RIC, DuBois and Mead models, it's necessary to use the nonlinear LS algorithm instead. The initial guesses of the parameter values were random, with a uniform distribution over the range of numbers between 0 and a value that was either 5, 0.5 or 0.05 depending on whether the parameter was a resistance, capacitance or inductance, respectively. A total of at least twenty-five guesses and estimation runs were performed for each test data: the number of guesses and runs increased as the model became more complex.

Table 1 shows the estimation errors obtained for each model for one patient's data (inclusive of post-mannitol responses). In the case of this patient, it is seen that augmented RIC model provides the best fit, followed closely by Mead's model, while the RIC model provides the worst fit. As an illustration, FIGS. 7A and 7B compare the respiratory impedance ($Z_R$ and $Z_X$) for this patient, as measured by IOS, to the impedance estimated from that one test's data for the extended RIC model and also the augmented RIC model (with the parameter values given in Table 2). Note that the augmented RIC model's real impedance shows an increase at the higher frequencies whereas the extended RIC model's real impedance does not. Table 2 also presents the parameter values estimated from the same IOS measurement for the other four models considered in this comparison. Note that the $C_l$ and $C_w$ estimates for the Mead model are quite large.

TABLE 1

Mean errors for all models: one patient in adult cohort 1

| Model | $Z_R$ LS error | $Z_X$ LS error | Total error |
|---|---|---|---|
| RIC model | 2.880424 | 0.528752 | 1.794190 |
| Ext. RIC model | 0.514334 | 0.102555 | 0.770101 |
| DuBois' model | 0.316112 | 0.077805 | 0.613176 |
| Mead's model | 0.059813 | 0.059967 | 0.312783 |
| Augmented model | 0.056308 | 0.058544 | 0.307021 |

TABLE 2

Estimated parameter values from an IOS measurement of one patient in adult cohort 1.

| Model | Estimated parameter values (with units of $cmH_2O/L/s$, $cmH_2O/L/s^2$, and $L/cmH_2O$ for resistances, inertances and compliances, respectively) |
|---|---|
| RIC model | R = 2.7599, I = 0.0063916, C = 0.011655 |
| DuBois' model | $R_{aw}$ = 2.4173, $I_{aw}$ = 0.0077980, $R_t$ = 5.2361, $I_t$ = 0.13735, $C_t$ = 0.0079216, $C_g$ = 0.0091930 |
| Mead's model | $R_c$ = 1.9601, $R_p$ = 4.7039, $C_l$ = 4518.2, $C_w$ = 751.56, $C_b$ = 0.0066670 $C_e$ = 0.00045589, I = 0.010772 |
| Ext. RIC model | R = 2.2358, $R_p$ = 5.4091, I = 0.0078989, C = 0.0080936 |
| Augmented model | R = 1.960, $R_p$ = 4.704, I = 0.01077, C = 0.006667, $C_e$ = 0.0004559 |

Figure 8:
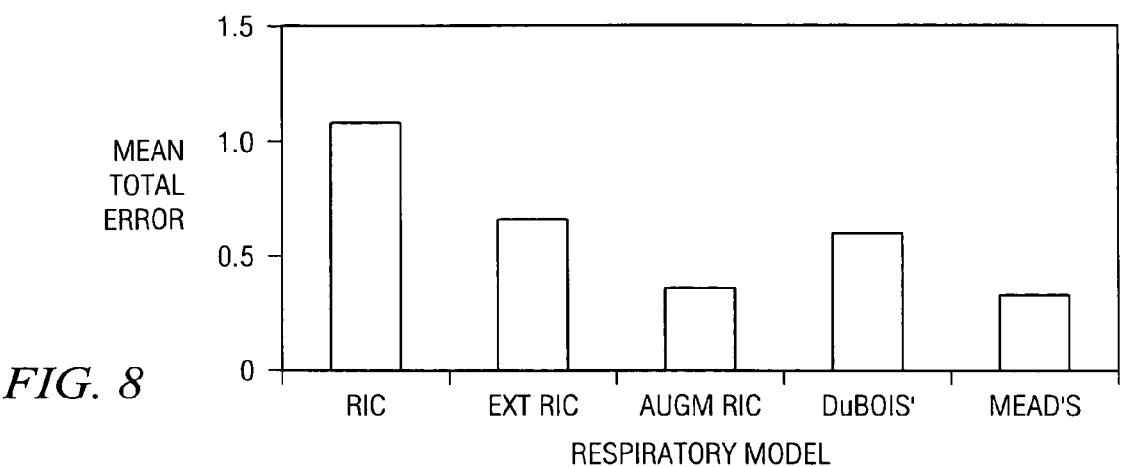
FIG. 8 is a graphical analysis of the mean total errors in selected patients for each circuit respiratory system model.

For the entire data set of 5 patients with mild airflow obstruction, obtained at baseline and after provocation by mannitol, Mead's model yielded the best fit (see Table 3 and FIG. 8) while the augmented RIC model was second best.

TABLE 3

Mean errors for all models: entire adult cohort 1 patient data set

| Model | Mean $Z_R$ LS error | Mean $Z_X$ LS error | Mean total error | Total error std deviation |
|---|---|---|---|---|
| RIC model | 1.2722 | 0.2612 | 1.0854 | 0.5961 |
| Ext. RIC model | 0.4132 | 0.0967 | 0.6807 | 0.2157 |
| Augmented RIC | 0.0510 | 0.0683 | 0.3257 | 0.1152 |
| DuBois' model | 0.2209 | 0.1630 | 0.5891 | 0.1919 |
| Mead's model | 0.0381 | 0.0611 | 0.2927 | 0.1165 |

In examining these more general results, it is important to note that a significant proportion of the estimates, for each particular model and patient, converged to the same values although their initial guesses were different. This suggests a global minimum was reached in these cases. Furthermore, while Mead's model yielded minimal errors, it more often than not produced unrealistically large estimates for lung compliance C, (a majority being larger than 5000 $L/cmH_2O$ with mean and standard deviation of 11219 $L/cmH_2O$ and 28598 $L/cmH_2O$, respectively), given that these patients had mild airflow obstruction, and also for chest wall compliance $C_w$ (a majority being larger than 500 $L/cmH_2O$ with mean and standard deviation of 15074 $L/cMH_2O$ and 75455 $L/cmH_2O$, respectively). In contrast, the R and $R_p$ values for the augmented RIC model (where R is analogous to central airway resistance) are more in line with what is expected in these patients with mild airflow obstruction. Moreover, the values for C estimated from the augmented RIC model are roughly comparable to what would be expected of capacitance of the small airways in these patients.

It may also be noted that while the DuBois model provided the third lowest mean total error in this comparison, the importance of reactance $Z_X$ should not be overlooked, as current clinical research has shown the pre-eminence of reactance parameters as being most sensitive to small airway obstruction in patients with chronic airflow obstruction. Thus, the augmented RIC model's total error was slightly less than the DuBois model, and equally important, the reactance error was also less for the augmented RIC, which is to its advantage. In addition, several estimates for the DuBois model's tissue compliance $C_t$ were larger than 9 $L/cmH_2O$ (with mean and standard deviation of 5.9 $L/cmH_2O$ and 49 $L/cmH_2O$, respectively).

Figure 9:
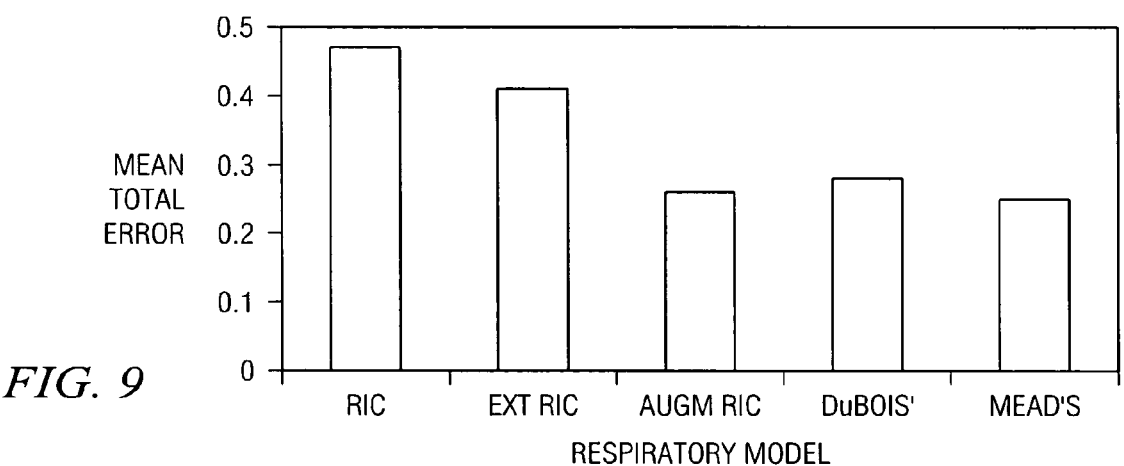
FIG. 9 is another graphical analysis of the mean total errors in selected normal patients for each circuit respiratory system model.

The data for the group of 5 adults with no known respiratory disease were also analyzed. In this case, Mead's model again yielded the lowest mean total error value followed by the augmented model, while the RIC model again provided the worst fit (Table 4 and FIG. 9). However, many of the Mead model estimates for lung compliance $C_l$ and for chest wall compliance $C_w$ were again unreasonably large (with means of 6541 $L/cmH_2O$ and 928 $L/cmH_2O$, respectively).

TABLE 4

Mean errors for all models: entire adult cohort 1 normal subject data set

| Model | Mean $Z_R$ LS error | Mean $Z_X$ LS error | Mean total error | Total error std deviation |
|---|---|---|---|---|
| RIC model | 0.1829 | 0.0551 | 0.4748 | 0.1124 |
| Ext. RIC model | 0.1253 | 0.0442 | 0.4052 | 0.0728 |
| Augmented RIC | 0.0312 | 0.0434 | 0.2596 | 0.0846 |
| DuBois' model | 0.0623 | 0.0218 | 0.2811 | 0.0603 |
| Mead's model | 0.0206 | 0.0397 | 0.2374 | 0.0627 |

Figure 10:
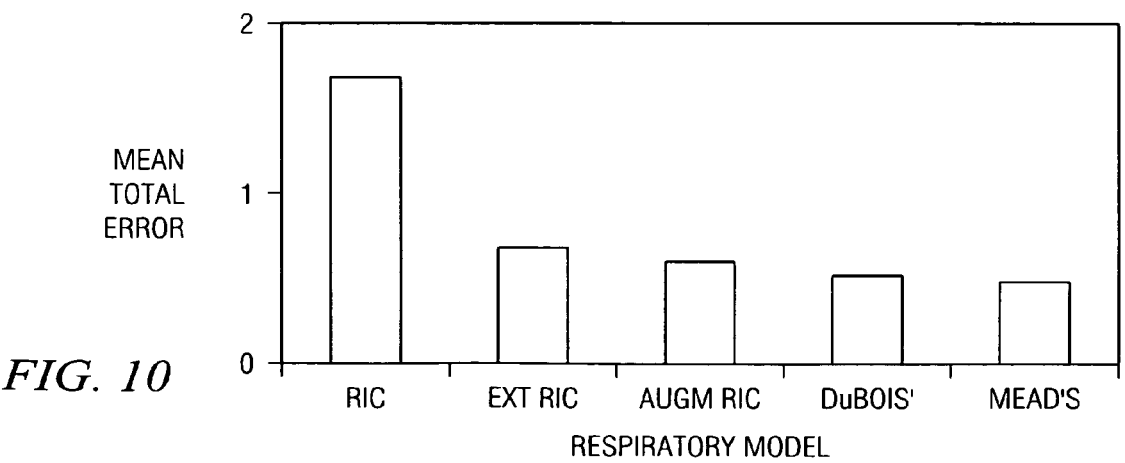
FIG. 10 is yet another graphical analysis of the mean total errors in differently selected patients for each circuit respiratory system model.

In addition to the data for these 10 adults, a second set of adult data that had been collected a few years ago in Australia was used for model parameter estimation. These 105 adults (to be referred to collectively as cohort 2) were all diagnosed with a respiratory disorder of either obstructive or restrictive type, including asthma, chronic obstructive pulmonary disease (COPD) and sarcoidosis. The data consists of only one baseline test result per patient and so did not include any deliberately provoked responses. Table 5 and FIG. 10 shows Mead's model yielding the best fit, followed by DuBois model and then the augmented RIC model. But many unreasonably large estimates for the Mead model's lung compliance $C_l$ and chest wall compliance $C_w$ (with means of 5131 L/cmH$_2$O and 253 L/cmH$_2$O, respectively), and for the DuBois model's tissue compliance $C_t$ (with mean of 198 L/cmH$_2$O), were obtained once again.

TABLE 5

Mean errors for all models: entire adult cohort 2 patient data set

| Model | Mean $Z_R$ LS error | Mean $Z_X$ LS error | Mean total error | Total error std deviation |
|---|---|---|---|---|
| RIC model | 3.0166 | 0.5816 | 1.6551 | 0.9255 |
| Ext. RIC model | 0.2859 | 0.1570 | 0.6263 | 0.2310 |
| Augmented RIC | 0.2115 | 0.1578 | 0.5596 | 0.2371 |
| DuBois' model | 0.1454 | 0.0965 | 0.4586 | 0.1758 |
| Mead's model | 0.0985 | 0.1159 | 0.4343 | 0.1597 |

Note that the improvement in total error performance of the augmented RIC model compared to the extended RIC model for the first, second and third groups ranged from 10.86% to 83.03% (mean 49.84%), 13.34% to 63.67% (mean 36.19%) and 0% to 58.39% (mean 11.18%), respectively.

Based on a comparison of the parameter estimation errors for the proposed augmented RIC model of adult respiratory impedance and the four other models, it has been shown that Mead's model yielded the least estimation errors for the given data sets of normal adults, adults with mild chronic obstructive pulmonary disease and adults with various obstructive and restrictive respiratory disorders. But while Mead's model yielded minimal errors, it also usually produced unrealistically large estimates for lung compliance and for chest wall compliance. In contrast, the augmented RIC model's parameter estimates were more in line with what is expected in these patients and normal subjects.

Figure 12:
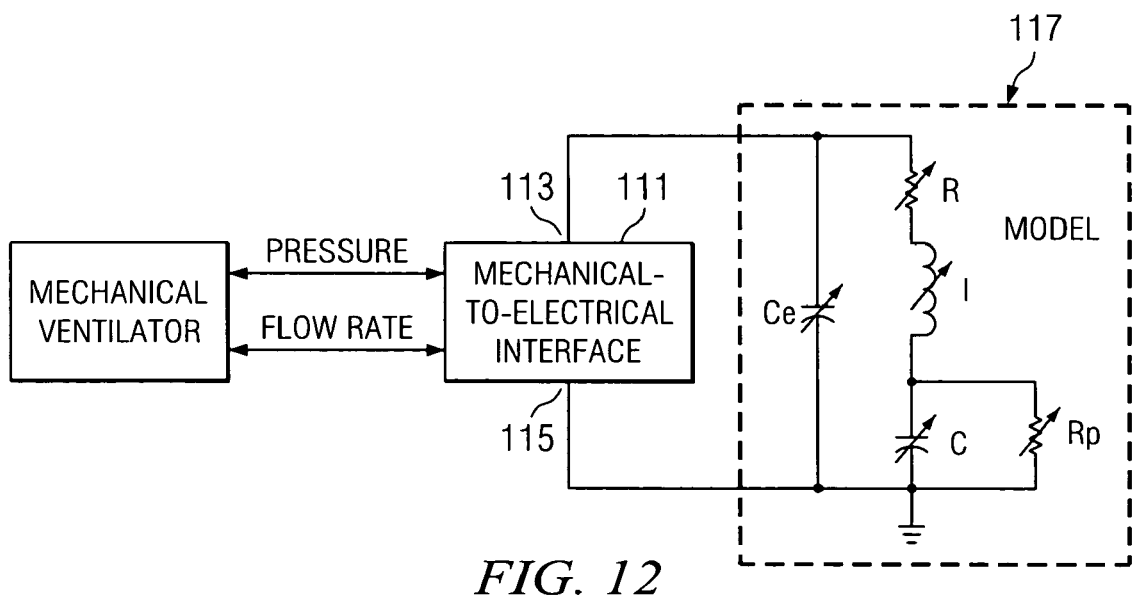
FIG. 12 is a block diagram of one example of the use of the respiratory impedance model of the invention.

Turning to FIG. 12, a block diagram is shown outlining one example of a use of the augmented RIC model of the present invention. A mechanical-to-electrical interface 111 is connected across the first and second terminals 113, 115, respectively, of the linear network 117 of the augmented RIC model. The interface may then be used to supply pressure and air flow rate values to an external device, such as a mechanical ventilator 119. In such an arrangement, the apparatus of the invention could be used, for example, by medical personnel to provide a starting point for the calibration of the ventilator, while eliminating the need to provide a human patient during the initial calibration stage.

An invention has been provided with several advantages. The additional electrical components used in the linear network of the invention provide an improved circuit model that takes into account the peripheral resistance of the respiratory system's small airways and extrathoracic compliance. By taking into account the small airway resistance and extrathoracic compliance components of the respiratory system, the improved linear network provides a viable alternative to the previous respiratory models known in the prior art. The present invention further minimizes the differences between the measured impedance data and the impedance produced by the model parameter values while providing an accurate and reliable model that can be used to detect, diagnose and assess the treatment of various pathologies. Furthermore, the method of analyzing a subject's air pressure and air flow that is non-invasive used in the present invention is easily administered to subjects of all ages and health.

The present invention has been described in terms of the preferred embodiment, and it is recognized that equivalents, alternative, and modifications, aside from those expressly stated, are possible and within the scope of the appending claims.

What is claimed is:

1. A respiratory impedance model for use in analyzing impulse oscillometry data for a human subject, comprising:
a linear network of electrical components connected in series between first and second terminals, wherein the components have a first resistance, a first inductance and a first capacitance respectively corresponding to a central resistance of airways, a lung inertance and an alveoli compliance of the human subject's respiratory system;
a second resistance component connected directly across the first capacitance component and corresponding to a peripheral resistance of alveoli in small airways of the human subject's lungs; and
a second capacitance component connected between the first and second terminals corresponding to an extrathoracic compliance parameter of the human respiratory system.

2. The respiratory impedance model of claim 1, wherein the linear network is configured as an assembly of physical components supported on a frame.

3. The respiratory impedance model of claim 2, wherein each of the physical components is adjustable within a range of parameter values.

4. The respiratory impedance model of claim 1, wherein the first and second terminals are connectable to a signal generator and an instrument for measuring complex impedance.

5. The respiratory impedance model of claim 1, wherein the linear network is constructed using a computer program and is as a virtual network represented in graphical form, and wherein the computer operates using program instructions to estimate values of the resistance, inductance, and capacitance.

6. The respiratory impedance model of claim 1, wherein the linear network is constructed using a computer program and is configured as a virtual network represented in graphical form, and wherein the computer operates using program instructions to adjust values of the resistance, inductance, and capacitance.

* * * * *